Figure 1:
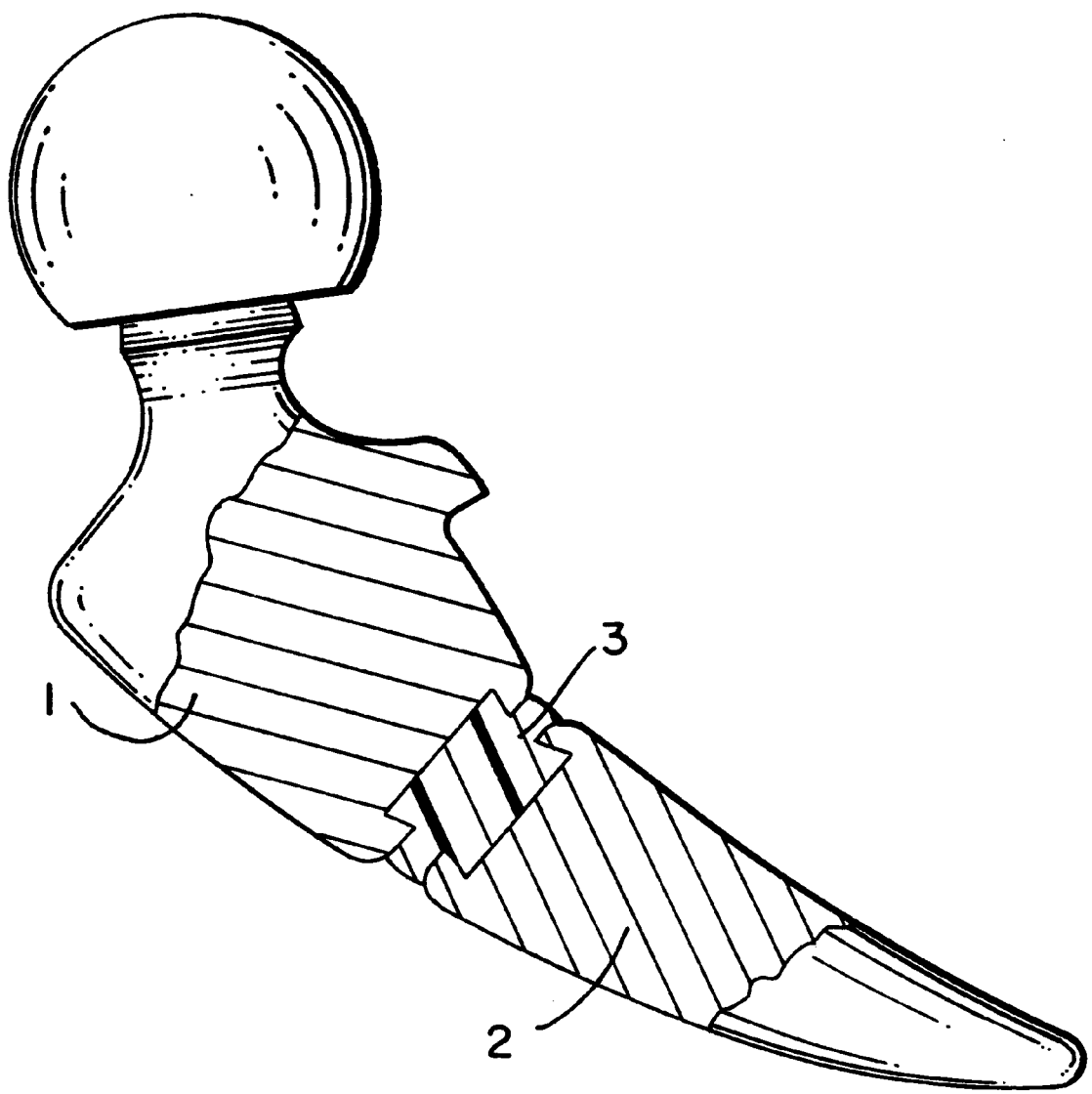

United States Patent [19]
Lampe et al.

[11] Patent Number: 6,071,312
[45] Date of Patent: Jun. 6, 2000

[54] ENDOPROSTHESIS, IN PARTICULAR AN ARTIFICIAL HIP JOINT

[76] Inventors: Frank Lampe, Geschwister-Scholl-Strasse 83, 20251 Hamburg; Roman Nassutt, Stettiner Strasse 18, 23879 Mölln, both of Germany

[21] Appl. No.: 09/011,438
[22] PCT Filed: Aug. 8, 1996
[86] PCT No.: PCT/EP96/03506
  § 371 Date: Feb. 13, 1998
  § 102(e) Date: Feb. 13, 1998
[87] PCT Pub. No.: WO97/06752
  PCT Pub. Date: Feb. 27, 1997

[30] Foreign Application Priority Data

Aug. 16, 1995 [DE] Germany .......................... 195 29 988
Aug. 19, 1995 [DE] Germany .......................... 195 30 531

[51] Int. Cl.[7] ................................................... A61F 2/36
[52] U.S. Cl. ............................................. 623/23; 606/77
[58] Field of Search ........................ 623/19, 23, 21; 606/77

[56] References Cited

U.S. PATENT DOCUMENTS 3,833,002  9/1974  Palma .
4,973,333  11/1990  Treharne ................................. 606/77
5,201,738  4/1993  Scott et al. ............................. 606/77
5,201,771  4/1993  Belykh et al. .......................... 623/23
5,735,901  4/1998  Maumy et al. ......................... 623/18

FOREIGN PATENT DOCUMENTS 0163121  12/1985  European Pat. Off. .
0176711  4/1986  European Pat. Off. .
0359485  3/1990  European Pat. Off. .
0603976  6/1994  European Pat. Off. .
8903850  6/1989  Germany .
41 37 383 A1  5/1993  Germany ............................. 623/23

*Primary Examiner*—David H. Willse
*Attorney, Agent, or Firm*—Friedrich Kueffner

[57] ABSTRACT

An endoprosthesis in the form of a hip joint has a stem and a joint part. The stem has a first individual stem part and a second individual stem part, wherein the first individual stem part has a first end connected to the joint part and a second end facing the facing end of the second individual stem part. A connection element made of bioresorbable material connects the second end of the first individual stem part and the facing end of the second individual stem part. When the endoprosthesis is implanted, the connection element is gradually resorbed so that the first and second individual stem parts become mechanically decoupled and load is introduced into the bone only via the first individual stem part now ingrown into the bone.

5 Claims, 2 Drawing Sheets

ENDOPROSTHESIS, IN PARTICULAR AN ARTIFICIAL HIP JOINT

The invention is directed to a hip joint prosthesis comprising a stem and a joint part.

Joint endoprostheses replace joints that have been damaged through degenerative, inflammatory, traumatic or tumorous changes and thus make it possible for the patient to lead a substantially normal life.

As is well known, the ideal joint implant should enable physiologic proximal-metaphyseal load transfer in the weight-bearing bone portion. For adequate fixation, especially for the primary fixation of cementless implants, conventional implants, especially in the hip area, have a prosthesis stem which extends far into the marrow space of the weight-bearing bone.

It is further known that the required physiologic introduction of load is changed as a result of the conventional long-stem prosthesis such that distal diaphyseal introduction of force is benefitted instead of proximal-metaphyseal introduction of force (Menge, M. 1994, Die metaphysäre Prothesenverankerung—ein neues Konzept für die Femurprothese [Metaphyseal Prosthesis Fixation—a new concept for femur prosthesis]). As a result of this redirection of force into the distal region of the weight-bearing bone (femur), there is a reduction of mechanical stress on the bone in the proximal region, referred to as stress-shielding. This results in the frequently observed resorption of bone in the proximal region, especially of the calcar (calcar atrophy). In addition, an increased introduction of force is caused distally in the stem tip region with resulting cortical hypertrophy (Cohen, C., Rushton, N., 1995, Bone Remodelling in the Proximal Femur After Charnley THA), (Kuiper, J. H., 1993, Three-Dimensional Optimization of Hip Prosthetic Design). These mechanisms lead to loosening of the prosthesis in the bone bearing portion and accordingly to failure of the implant.

It is further known that the loss of bone matter in cases of a replacement operation makes the fixation of the replacement prosthesis considerably more difficult and often requires the use of expensive special implants.

It is further known that known copolymers, for example, those produced from D,L-lactide or L-lactide or from glycolide or from a mixture of these materials, can be used as bioresorbable materials. Further, self-reinforced materials have been developed which are far superior to previous materials with respect to their mechanical properties. These materials are already used in the manufacture of bone screws, bone pins and bone plates, see, e.g., Törmälä, P. 1993, Ultra-high Strength, Self-Reinforced Absorbable Polymeric Composites for Applications in Different Disciplines of Surgery, Clin. Mat. pp. 35–40.

It is further known that the resorption of large amounts of bioresorbable material in the body can lead to undesirable foreign body reactions.

The object of the invention is to minimize the frequency of prosthesis replacement operations arising from loosening of the prosthesis; these operations are complicated in technical respects relating to organs, expensive, and burdensome to the patient.

This object is fundamentally met by the upper stem part and the lower stem art being connected by means of a connection-element manufactured from bioresorbable material.

A particularly advantageous embodiment form has a second connection element made from non-resorbable material, for example, high quality steel, and arranged in the region of the first connection element, made from bioresorbable material.

The advantages achieved by the invention consist in that this type of prosthesis, due to its long stem, ensures sufficient is primary stability appropriate for current prosthetic variants in the period immediately following the operation. Through the progressive decomposition of the bioresorbable intermediate piece in the weeks following the operation, a continuous or steady mechanical decoupling of the distal stem part from the proximal stem part is achieved, resulting in a reduced mechanical loading of the distal stem part. Bony ingrowth of the proximal stem part occurs simultaneously. This process then leads to an exclusively proximal fixation or anchoring and accordingly to a physiologic introduction of load into the bone bearing portion. Aseptic loosening of implants which is triggered by mechanically induced bone resorption processes can accordingly be prevented. This makes possible an appreciable increase in the life of the prosthesis.

In the event that a replacement operation should become necessary for other reasons, a solid starting position is provided for the fixation of the replacement prosthesis by the preservation of the proximal bone matter.

The functions of the new hip endoprosthesis described herein are achieved with a small material volume of the intermediate piece. This has decisive importance because larger amounts of bioresorbable material in the body can lead to undesirable tissue responses or reactions.

In one embodiment, there is provided, in addition to the connection element made of bioresorbable material, another connection element produced from non-resorbable material, for example, high-quality steel, which provides for mechanical support. However, this additional connection element does not transmit any bending forces.

The invention will be explained more fully hereinafter with reference to the drawing and an embodiment example.

Figure 2:
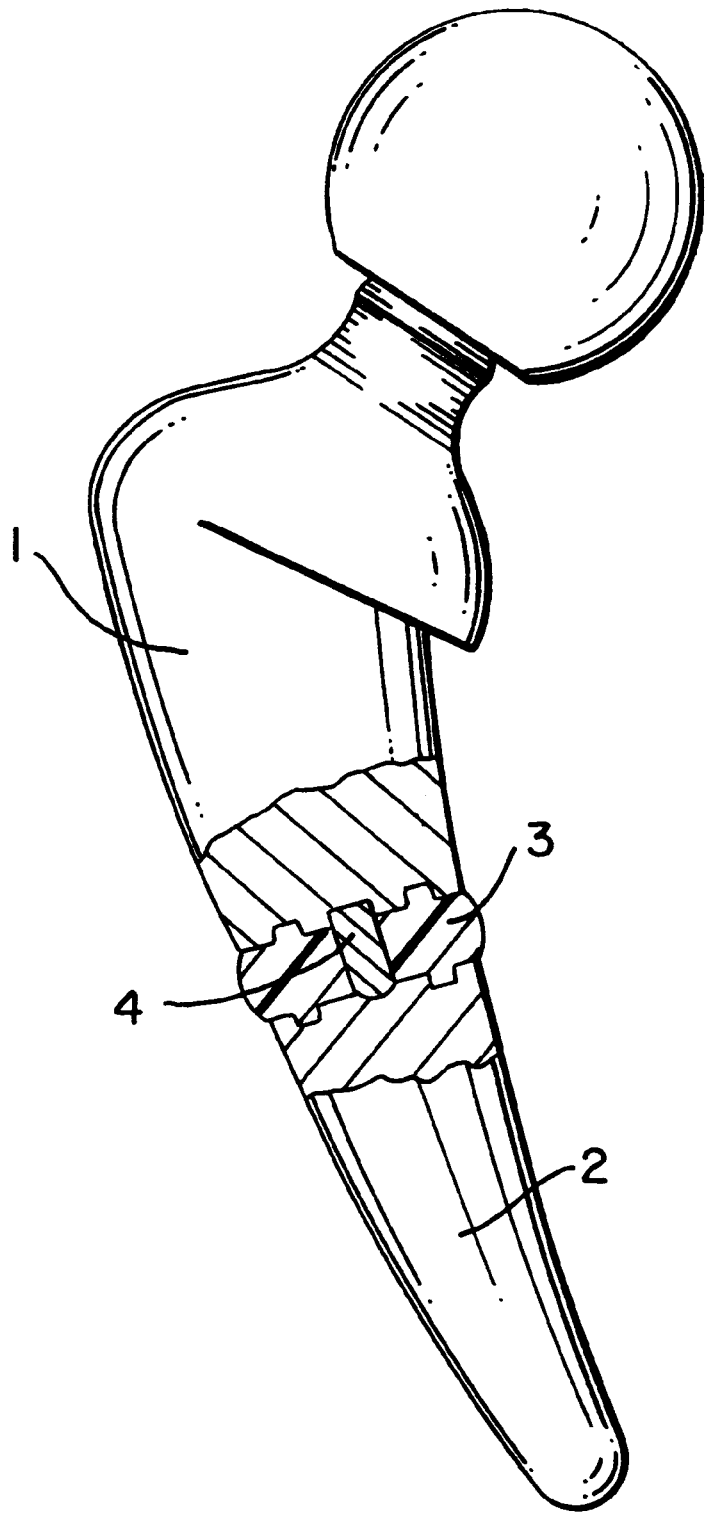

FIG. 1 shows a section through a first embodiment form of a hip joint prosthesis according to the invention; and FIG. 2 shows a section through another embodiment form of a hip joint prosthesis according to the invention.

The hip joint prosthesis shown in FIG. 1 has an upper part 1 and a lower part 2. A connection element 3 fabricated from bioresorbable material is arranged between these two parts 1 and 2.

This hip joint prosthesis resists possible loosening through bone remodelling processes. Through the decomposition of the bioresorbable intermediate piece in the prosthesis stem, there occurs a continuous mechanical decoupling of the distal stem part from the proximal stem part. In this way, the distal stem part is relieved of mechanical loading and a natural introduction of load into the bone is achieved only along the bony ingrown proximal stem part. The primary stability required immediately after the operation is ensured nevertheless. In principle, it is possible to use not only as a hip joint prosthesis, but also in all tubular or long bones, e.g., the knee, elbow and finger.

In the embodiment form according to FIG. 2, another connection element 4 produced from non-resorbable material, for example, high-quality steel, is provided in the region of the bioresorbable connection element 3. This additional connection element 4 is arranged and constructed in such a way that it cannot transmit any bending forces, but provides for an additional absorption of compressive forces in the axial direction. It can be fastened in the upper part 1 of the shaft or shank and can be supported in the lower part 2 so as to be articulated in the manner of a socket. Other types of fastening are possible.

We claim:

1. Endoprosthesis comprising a stem and a joint part, the stem comprised of a first individual stem part and a second individual stem part, wherein the first individual stem part has a first end connected to the joint part and a second end facing a facing end of the second individual stem part, further comprising a connection element made of bioresorbable material configured to connect the second end of the first individual stem part and the facing end of the second individual stem part.

2. Epdoprosthesis according to claim 1, further comprising a second connection element, made of non-resorbable material, arranged in the region of the first connection element and configured to additionally connect the second end of the first individual stem part and the facing end of the second individual stem part.

3. Endoprosthesis according to claim 2, wherein the second connection element is configured to transmit compressive force acting substantially in the axial direction of the stem but not transmit any bending forces between the first individual stem part and the second individual stem part.

4. Endoprosthesis according to claim 2, wherein the second connection element is made of high-quality steel.

5. Endoprosthesis according to claim 1 in the form of a hip joint prosthesis.

* * * * *